US012773358B2

(12) United States Patent
Hardie et al.

(10) Patent No.: US 12,773,358 B2
(45) Date of Patent: Oct. 27, 2026

(54) ABSORBENT ARTICLE WITH NARROW STABILIZATION ELEMENT

(71) Applicant: The Procter & Gamble Company, Cincinnati, OH (US)

(72) Inventors: Stephen Lebeuf Hardie, Mason, OH (US); Ronda Lynn Glassmeyer, Cincinnati, OH (US); Fred Naval Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 283 days.

(21) Appl. No.: 18/589,495

(22) Filed: Feb. 28, 2024

(65) Prior Publication Data

US 2024/0285448 A1 Aug. 29, 2024

Related U.S. Application Data

(60) Provisional application No. 63/448,813, filed on Feb. 28, 2023.

(51) Int. Cl.
*A61F 13/53* (2006.01)
*A61F 13/515* (2006.01)

(52) U.S. Cl.
CPC ............ *A61F 13/53* (2013.01); *A61F 13/515* (2013.01)

(58) Field of Classification Search
CPC ...... A61F 13/53; A61F 13/515; A61F 13/531; A61F 13/53747; A61F 13/15203; A61F 2013/15406; A61F 2013/5315
See application file for complete search history.

(56) References Cited

U.S. PATENT DOCUMENTS

| | | | | |
|---|---|---|---|---|
| 5,716,703 | A * | 2/1998 | Payne | A61F 13/53747 604/378 |
| 2002/0177829 | A1 | 11/2002 | Fell | |
| 2007/0016153 | A1 | 1/2007 | Hird et al. | |
| 2015/0173967 | A1 | 6/2015 | Kreuzer | |
| 2020/0060891 | A1 | 2/2020 | Garcia et al. | |
| 2020/0306105 | A1 | 10/2020 | Peri et al. | |
| 2020/0315861 | A1 | 10/2020 | Viens | |

(Continued)

FOREIGN PATENT DOCUMENTS

| | | |
|---|---|---|
| JP | 2020028677 A | 2/2020 |
| WO | 0145610 A1 | 6/2001 |

OTHER PUBLICATIONS

PCT Search Report and Written Opinion for PCT/US2024/017654 dated Jun. 6, 2024, 14 pages.

(Continued)

*Primary Examiner* — Philip R Wiest
(74) *Attorney, Agent, or Firm* — Daniel S. Albrecht

(57) ABSTRACT

An absorbent article having a longitudinal centerline extending in a longitudinal direction and a transversal centerline extending in a transversal direction orthogonal to the longitudinal direction and bisecting the absorbent article in a front half and back half is presented. The absorbent article includes a liquid permeable topsheet on a wearer-facing side, a liquid impermeable backsheet on a garment-facing side, an absorbent core, and a stabilization element. The stabilization element has a width (W2) of 50 mm or less, as measured at the point C disposed 40 mm towards the front of the article from the transversal centerline.

15 Claims, 6 Drawing Sheets

(56) References Cited

U.S. PATENT DOCUMENTS

| | | | | |
|---|---|---|---|---|
| 2020/0405548 | A1* | 12/2020 | Li | A61F 13/539 |
| 2021/0161731 | A1* | 6/2021 | Van Malderen | A61F 13/515 |
| 2021/0186772 | A1 | 6/2021 | Sillerström et al. | |
| 2022/0023116 | A1 | 1/2022 | Schuberth et al. | |
| 2022/0168158 | A1 | 6/2022 | Miller et al. | |
| 2022/0257435 | A1 | 8/2022 | Miller et al. | |
| 2022/0265488 | A1 | 8/2022 | Chmielewski et al. | |
| 2022/0280350 | A1 | 9/2022 | Sartini et al. | |
| 2023/0039880 | A1 | 2/2023 | Van Ingelgem et al. | |
| 2024/0285449 | A1 | 8/2024 | Hardie | |

OTHER PUBLICATIONS

All Office Actions; U.S. Appl. No. 18/589,505, filed Feb. 28, 2024.

U.S. Appl. No. 18/589,505, filed Feb. 28, 2024, to Stephen Lebeuf Hardie et al.

* cited by examiner

ABSORBENT ARTICLE WITH NARROW STABILIZATION ELEMENT

CROSS REFERENCE TO RELATED APPLICATION

This application claims the benefit of U.S. Provisional Application No. 63/448,813, filed Feb. 28, 2023, the substance of which is incorporated herein by reference.

FIELD OF THE INVENTION

The present invention relates to personal hygiene absorbent articles. The articles may be in particular adult incontinence ("AI") products, such as light adult incontinence pants.

BACKGROUND OF THE INVENTION

In recent years, populations in many countries have shifted toward middle-aged and older demographic groups. These demographic groups represent markets with relatively increased demands for products and services addressed to concerns associated with aging. One such concern is adult urinary incontinence ("AI"). Urinary incontinence can result from or be exacerbated by a variety of health conditions, or even normal experiences such as childbearing.

Disposable absorbent pants for persons suffering from urinary incontinence have been marketed for a number of years. These products have traditionally been larger version of disposable baby diaper pants. One design type is known as the "belted" or "balloon" type pant, which is formed of a broad belt that encircles the wearer's waist and lower torso, bridged by an absorbent pad assembly that connects front and rear belt portions through the wearer's crotch area. The crotch absorbent pad assembly includes an absorbent core designed to receive, contain and store urine until the time the pant is changed. The belt is typically formed of a stretch laminate material.

The absorbent material in the absorbent core is typically a mixture of cellulose fibers and superabsorbent polymer (SAP) particles, which is susceptible to bunching when lightly loaded with urine due to wet collapse of the pulp fibers. This is particularly problematic in AI as the products are worn in the lightly loaded state much of the time (whereas heavily loaded article will be changed quickly).

Investigations into AI consumer's behaviors have shown that the primary drivers of consumer preference during use are comfort and fit, while leakage protection is a secondary driver. It is believed that this is due to consumers viewing the purchase of adult incontinence (at least outside of institutions) as an insurance policy in the event of a larger unintentional urine loss ("UUL"). However, due in part to mitigation strategies (such as frequent trips to the restroom), consumers on AI products rarely have large UUL's. Instead they typically suffer small losses of urine. Hence, adult wearers are for the most part wearing AI products while dry, or mostly dry, unlikely baby diapers. Adult wearers will also typically change the product as quickly as possible if heavily loaded. Since the incontinence product is worn for long periods of time without any, or much, UUL, the priority for the consumer is a more underwear like wearing experience (comfort and fit) vs. dryness and high absorbency over long periods of time like baby diapers.

The unintuitive result of this analysis is that a more ideal core design for AI product should rather focus on flexibility compared to other absorbent articles, and value the absorption of frequent small amounts of urine vs. large gushes. However, it was found that thin and flexible products are also more prone to become wrinkled or wedge in the crotch of the wearer. This increased wrinkling is believed to be due to product design favoring a wider absorbent assembly pad than the width of the wearer's crotch to enable sufficient absorbency. While increasing the thickness of the core can prevent the wrinkles, it may also be uncomfortable for the wearer.

SUMMARY OF THE INVENTION

The invention relates to a personal hygiene absorbent article. The article is notionally divided into a left half and right half by a longitudinal centerline extending in a longitudinal direction, and into a front half and a back half by a transversal centerline extending in a transversal direction orthogonal to the longitudinal direction. The absorbent article comprises a liquid permeable topsheet, a liquid impermeable backsheet and an absorbent core disposed between the topsheet and the backsheet. The absorbent core comprises a core wrap and an absorbent material layer disposed in the core wrap.

In order to address the problems described above, it was found that providing a narrow stabilization element at least in the crotch region of the absorbent article can reduce wrinkling where wrinkling is most noticeable both visually and tactilely. The stabilization element and the absorbent core are disposed between the topsheet and the backsheet and are superposed at least at a point C disposed at a distance of about 40 mm from the transversal centerline towards the front of the article and transversally aligned on the absorbent material layer of the absorbent core.

The stabilization element has a width at or close to this point C of no more than 50 mm as measured in the transversal direction according to the Width And Caliper Measurement Method described herein. The stabilization element may typically have a width in the range of from about 20 mm to about 50 mm, in particular from 20 mm to 40 mm, which was found to be sufficiently narrow to prevent pressure on the inner legs during walking or other activities while providing increased stability to the article.

The article may be an adult incontinence product. The absorbent article may be a belted adult incontinence pant, but other executions are possible such as a taped diaper. Exemplary dimensions, materials and properties of the stabilization element are further disclosed in the below description and appended claims with further aspects of the invention. The absorbent article may in particular further comprise any of the following elements individually or in combination.

The absorbent core is typically wider than the stabilization element, so that the absorbent core extends further transversally than the stabilization element. The absorbent core (including the absorbent material layer contained therein) preferably extends at least transversally 5 mm outboard of a point R and at least 5 mm outboard of a point L, the point R and L disposed respectively 30 mm right and left in the transversal direction of the point C. The stabilization element on the other hand preferably does not extend transversally to any of the points L and R.

The absorbent article may have a first caliper C1 at the point C, a second caliper C2 at point R and a third caliper C3 at point L (wherein the calipers are measured according to the Width and Caliper Measurement Method disclosed herein). The ratio C1/(C2+C3) may have a value of at least 0.6, in particular the ratio C1/(C2+C3) may be in the range of from 0.6 to 3.0, more particularly of from 0.65 to 1.0. The caliper C1 may be less than 5.0 mm. The average value (C2+C3)/2 may be less than 4.5 mm.

The stabilization element may have urine acquisition and/or distribution properties.

The stabilization element may comprise or consists of cross-linked cellulose fibers.

The stabilization element may comprise or consists of a spunlace layer.

The stabilization element may have a basis weight of from 50 gsm to 200 gsm.

The incontinence product may be an adult incontinence pant.

The absorbent material may consist essentially of superabsorbent polymers (but other absorbent materials are possible).

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DETAILED DESCRIPTION OF THE INVENTION

Definitions

Figure 1:
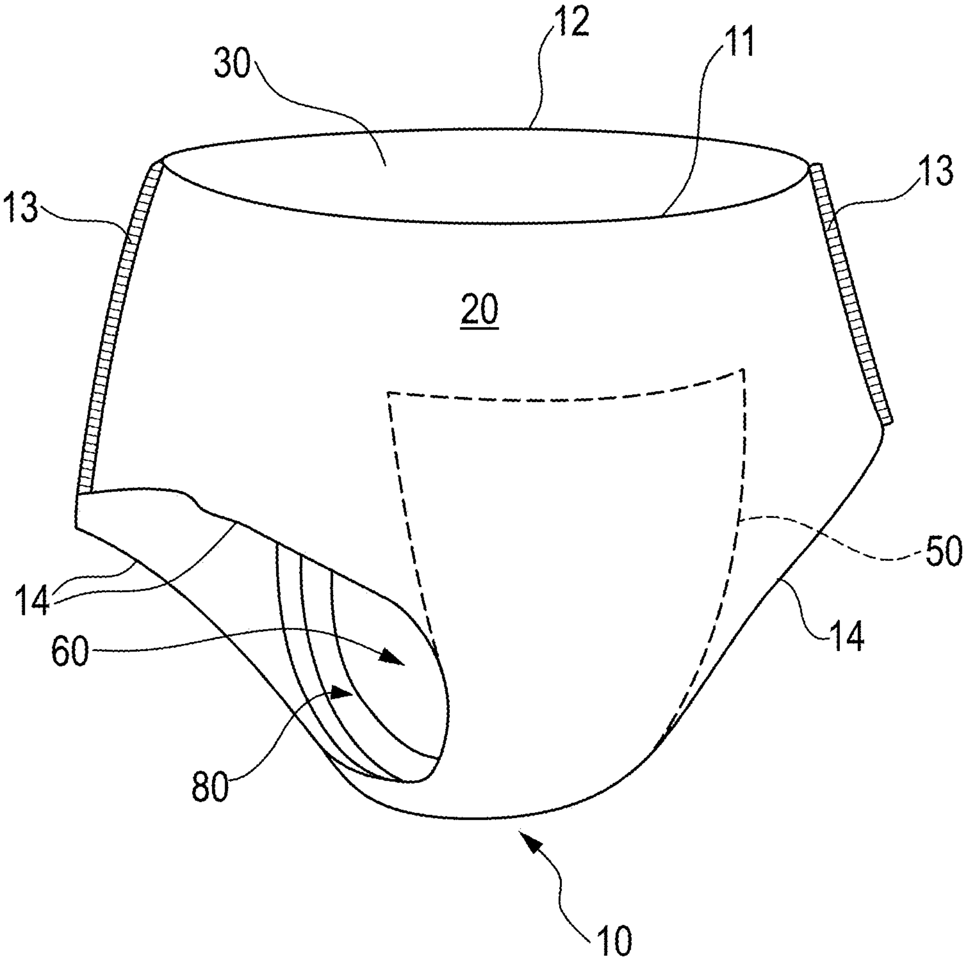
FIG. 1 is a schematic perspective view of an exemplary adult incontinence pant.

As used herein, the terms "nonwoven", "nonwoven web" and "nonwoven layer" are used interchangeably. Nonwovens are broadly defined as engineered fibrous assemblies, primarily planar, which have been given a designed level of structural integrity by physical and/or chemical means, excluding weaving, knitting or paper making.

Nonwovens can be formed by many processes such as meltblowing, spunlaying, solvent spinning, electrospinning, and carding, and the fibers can be consolidated, e.g. by hydroentanglement (in spunlace nonwoven), air-through bonding (using hot air that is blown through the fiber layer in the thickness direction), needle-punching, one or more patterns of bonds and bond impressions created through localized compression and/or application of heat or ultrasonic energy, or a combination thereof. The fibers may, alternatively or in addition, be consolidated by use of a binder. The binder may be provided in the form of binder fibers (which are subsequently molten) or may be provided in liquid, such as a styrene butadiene binder. A liquid binder is provided to the fibers (e.g., by spraying, printing or foam application) and is subsequently cured to solidify. The basis weight of nonwoven fabrics is usually expressed in grams per square meter ($g/m^2$).

Nonwoven materials can be formed by a variety of fiber materials (PP, PE, PET, coPET, bicomponent, natural fibers and mixture thereof). Synthetic fibers may be selected from the group consisting of polyolefins (such as polyethylene, polypropylene or combinations and mixtures thereof), polyethylene terephthalate (PET), co PET, polylactic acid (PLA), polyhydroxy alkanoid (PHA), or mixtures or combinations thereof. Natural fibers are for example cotton or bamboo fibers, or man-made origin. The fibers may be staple fibers (e.g., in carded nonwoven webs/layers) or continuous fibers (e.g., in spunbonded or meltblown nonwoven webs/layers). In some cases, the fibers or the nonwovens can be treated to enhance specific fluid handling characteristics, such as fluid permeability or fluid barrier properties.

The term "spunlace" or "spunlace nonwoven" means a nonwoven wherein the cohesion and the interlacing of the fibers with one another is obtained by means of a plurality of jets of water under pressure passing through a moving fleece or cloth and, like needles, causing the fibers to intermingle with one another. These spunlace nonwovens are essentially defined by the fact that their consolidation results from hydraulic interlacing. The spunlace may be single stratum (homogeneous), but spunlace nonwovens may also be formed of two or more strata having different fiber mixture composition, and which are combined with each other by hydraulic interlacing. The two or more strata, prior to being combined into one nonwoven by hydraulic interlacing, may have underdone bonding processes, such as heat and/or pressure bonding by using e.g., a patterned calendar roll and an anvil roll to impart a bonding pattern. However, the two or more strata are combined with each other solely by hydraulic interlacing.

The term "dtex" as used herein refers to a unit used to indicate the fineness of a filament/fiber. The unit expresses the mass of a filament/fiber in grams per 10,000 meters of length.

"Hydrophilic" describes substrates having surfaces which are wettable by aqueous fluids (e.g., a NaCl saline solution at 0.9% concentration) deposited on these substrates. Hydrophilicity and wettability are typically defined in terms of contact angle and the strike-through time of the fluids, for example through a nonwoven fabric. This is discussed in detail in the American Chemical Society publication entitled "Contact Angle, Wettability and Adhesion", edited by Robert F. Gould (Copyright 1964). A surface of a substrate is said to be wetted by a fluid (i.e., hydrophilic) when either the contact angle between the fluid and the surface is less than 90°, or when the fluid tends to spread spontaneously across the surface of the substrate, both conditions are normally co-existing. Conversely, a substrate is considered to be "hydrophobic" if the contact angle is greater than 90° and the fluid does not spread spontaneously across the surface of the fiber.

"Longitudinal" refers to a direction running perpendicular from the middle of a waist edge to the middle of an opposing waist edge of the article, notionally defined a longitudinal centerline. Absorbent articles are symmetrically constructed relative to this longitudinal centerline so that the longitudinal centerline divides the article in a left half and right half. "Transversal" refers to a direction perpendicular to the longitudinal direction, and the transversal centerline is the notional line perpendicular to the longitudinal centerline that divides the article in a front half and a back half of same length. As used herein, "longitudinally-extending" refers to a feature of the article extending at least twice as much in the longitudinal direction than in the transversal direction.

"Body-facing" and "garment-facing" refer respectively to the relative location of an element or a surface of an element or group of elements. "Body-facing" implies the element or surface is nearer to the wearer during wear than another element of the same component. "Garment-facing" implies the element or surface is more remote from the wearer during wear than another element of the same component. The garment-facing surface may face another garment of the wearer, or other items, such as the bedding, or the atmosphere.

"Comprise," "comprising," and "comprises" are open ended terms, each specifies the presence of the feature that follows, e.g., a component, but does not preclude the presence of other features, e.g., elements, steps, components known in the art or disclosed herein. These terms based on the verb "comprise" encompass the narrower terms "consisting essential of" which excludes any element, step or ingredient not mentioned which materially affect the way the feature performs its function, and the term "consisting of" which excludes any element, step, or ingredient not specified.

Absorbent Article

As used herein, the term "absorbent article" refers to a personal hygiene absorbent article that is placed in the crotch region of a wearer to absorb exudates discharged from the body, in particular urine. The absorbent articles of the invention can in particular be placed about the lower torso of the wearer so as to encircle the waist and legs of the wearer. The absorbent article of the invention may be in particular a pant article, having the waist opening and the leg openings pre-formed by left and right seams at the edges of the pant article. A pant article may be pre-formed by any suitable techniques including, but not limited to, joining together portions of the absorbent article using re-fastenable and/or non-refastenable bonds (e.g., seam, weld, adhesive, cohesive bond, fastener, etc.). A pant article may be pre-formed anywhere along the circumference of the article (e.g., side fastened, front waist fastened). The invention may also be used for other types of absorbent articles such as taped articles or sanitary napkins. In a taped article, the back half of the article can be releasably attached to the front half by a tape system. While the present invention is generally applicable to any types of absorbent articles, including baby or infant diapers, it is in particular suitable for adult incontinence pant article.

Brief Description of an Incontinence Pant 10

FIG. 1 depicts an example of a belt- or balloon-type disposable absorbent pant 10. The pant 10 has a waist opening defined by a front waist edge 11 and rear waist edge 12 and a pair of leg openings defined by respective leg opening edges 14. The pant 10 includes a belt structure having a front panel 20 and a rear panel 30, which are joined at side seam areas 13. Typically, side seams are formed by welding/thermal bonding in which polymer materials in the front and rear panels are fused together at their edges by application of a combination of heat and pressure. The pant 10 may also include an absorbent pad assembly 50 extending between the front and back panels through a crotch region of the pant. The absorbent pad assembly 50 may be adhesively bonded to the inner surfaces of front and rear panels, typically a hotmelt adhesive is applied during the manufacturing process for this purpose. The front belt 20 and the back belt 30 typically comprise an elasticized laminate, such as a plurality of elastic threads 40 extending in the transversal direction and sandwiched between two nonwoven substrates.

Figure 2:
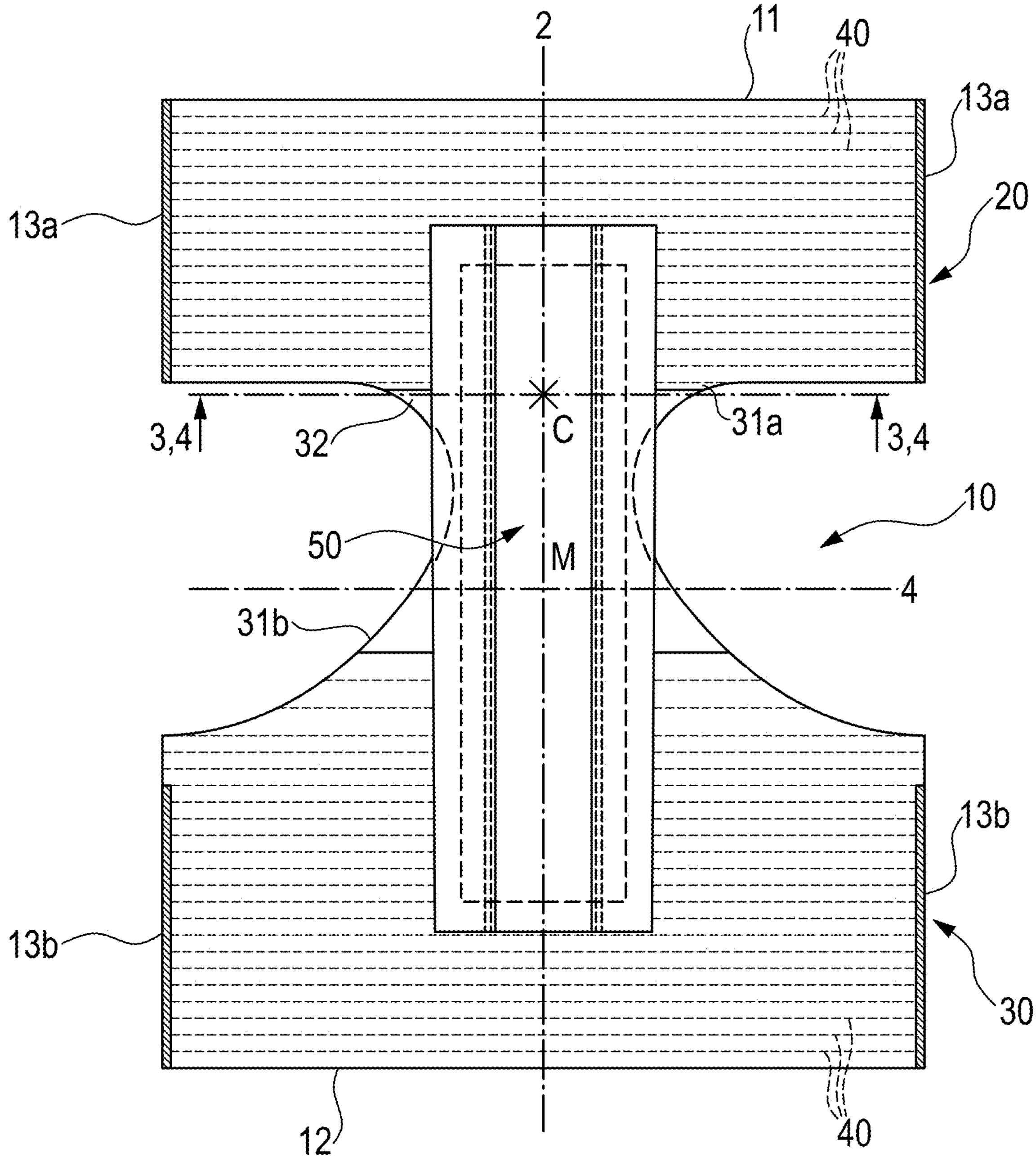
FIG. 2 is a schematic top view (wearer-facing surface) of the incontinence pant of FIG. 1, in a flat laid-out state with the side seams opened and showing the absorbent pad assembly disposed between the front belt and back belt.

FIG. 2 shows the pant article of FIG. 1 with the side seams 13*a,b* opened so that the article can be shown flattened out with the wearer-facing side of the pant shown. As shown in FIG. 2, the article extends in a longitudinal direction visualized by the longitudinal centerline 2 and a transversal direction visualized by transversal centerline 4. The longitudinal centerline extends from the middle of the edge of the front belt to the middle of the edge of the rear belt, and notionally divides the article in a left half and a right half, which are substantially symmetrical. The transversal centerline 2 is disposed in the crotch portion of the article and divides the article in a front half and a rear half having an equal length as measured along the longitudinal centerline 2. The intersection of the longitudinal centerline 2 and transversal centerline 4 is defined herein as the midpoint M.

Referring further to FIG. 2, the pant 10 includes a belt structure including front panel 20 and rear panel 30. In the example depicted, the outer layers of the front and rear panels comprise a continuous layer 32 common to both panels. The continuous layer 32 also wraps about the outside of the pant through the crotch region; this configuration is sometimes called a "unibody" construction. The outer layer(s) 32 is typically a nonwoven layer. In another possible configuration (not shown), front panel 20 and rear panel 30 panels may have discrete, separate outer layers, have no layer in common, and are joined only by the side seams 13 and the absorbent pad assembly. This alternative configuration is sometimes called a "multipiece" construction.

Each of the front and rear panels may comprise one or more elastic members, in particular a plurality of transversally extending strands 40 of an elastomeric material laminated between an inner belt layer (not shown) and an outer belt layer 32, such as elastane threads (for example, LYCRA HYFIT fiber, a product of Invista, Wichita, Kansas). The inner and outer belt layers may respectively be joined together about the elastic strands 40 by adhesive deposited between the layers, by thermal bonds, by compression bonds, or by a combination thereof. In other examples, the one or more elastic members may be strips or a section of film formed of elastomeric material. Elastic strands rather than film, however, may be preferred for the flexibility they provide by enabling individualized setting of pre-strain levels, selecting and setting uniform or varying longitudinal spacing therebetween, and preserving a high level of vapor transmission (breathability) through the belt laminate, for purposes of coolness, comfort and skin health. This flexibility helps enable the manufacturer to enhance the fit of the pant structure about the varying contours and sizes of differing wearers' anatomies, and impart a cloth-like appearance to the belt laminate. For purposes herein, a "strand" is a member having a cross section perpendicular to its longest dimension, the cross section having an aspect ratio of largest dimension to smallest dimension no greater than 2, in an unstrained condition.

The elastic belt may also or alternatively comprise an elastomeric nonwoven. Further typical features of an incontinence pant article, in particular the belt/panel structure can be found for example in WO2018/09417A1 (Minoguchi et al.), WO2017/192992A1 (Desai et al.), and WO2016/115421A1 (Seitz et al.).

Absorbent Pad Assembly 50

Figure 3:
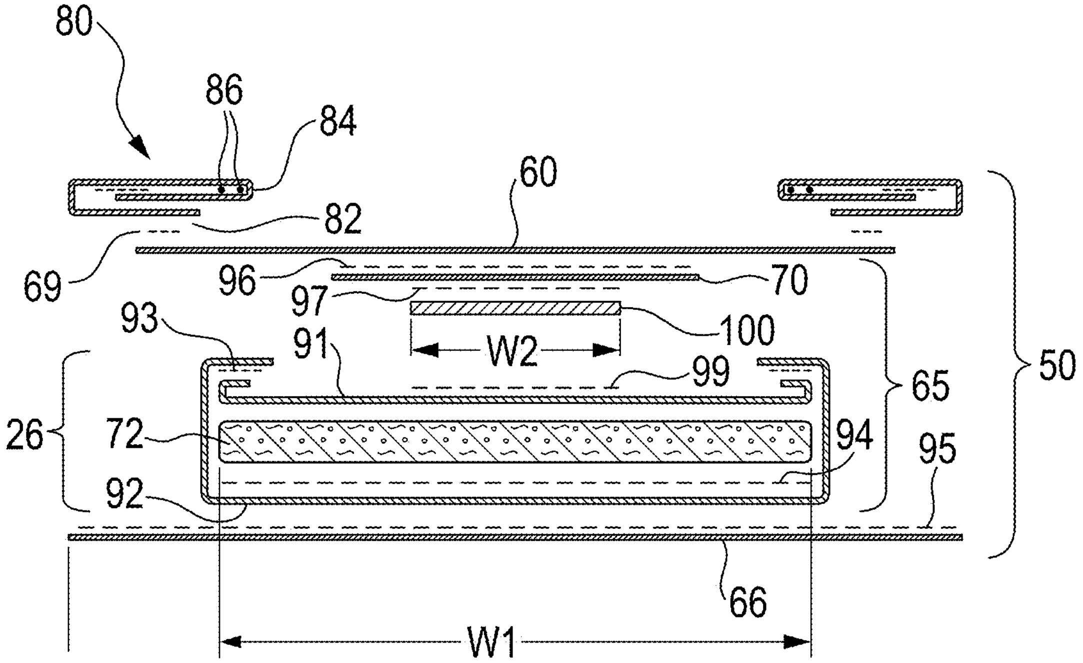
FIG. 3 is a schematic cross-section view of the absorbent pad assembly.
Figure 4:
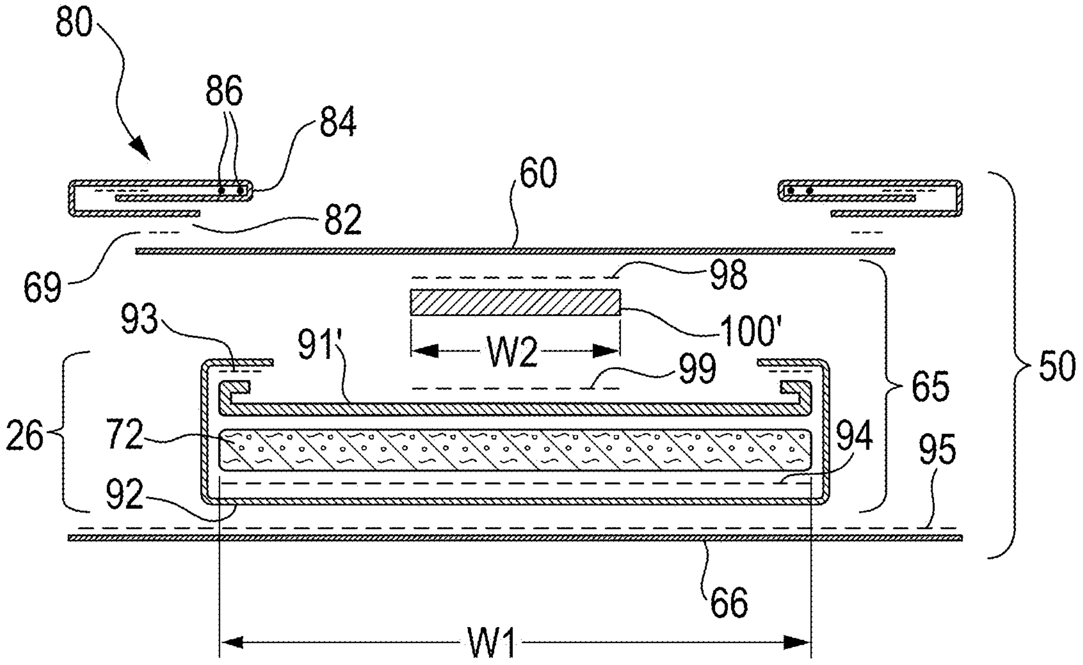
FIG. 4 is a schematic cross-section view of an alternative absorbent pad assembly.

The absorbent pad assembly 50, as illustrated in cross-section in FIGS. 3-4, may include a liquid permeable topsheet 60 on its wearer-facing side, a liquid impermeable backsheet 66 on its garment-facing side, a multi-component absorbent structure 65 including an absorbent core 26 disposed between the topsheet and the backsheet, and elasticized barrier leg cuffs 80. As described herein, additional features and combinations thereof may be included as well. Examples and descriptions of components and configurations of such an absorbent pad assembly may be found in WO2013/122936A1, wherein the central chassis described includes components and features that may be included.

The topsheet 60 may be formed of a nonwoven web material suitably selected to contain the components of the absorbent structure 65 while permitting urine to freely pass therethrough, from the wearer-facing surface to the absorbent structure. The backsheet 66 may include or be formed at least in part of a polymeric film material suitably selected to contain the components of the absorbent structure, and also to contain and prevent passage of urine from the absorbent structure therethrough to the garment-facing surface, under ordinary conditions of use. In some examples, the backsheet 66 may also include an outer layer formed of a nonwoven web material to provide added strength and impart a more cloth-like feel. In some examples, the backsheet film may be formed so as to be breathable, such that it can permit water vapor to pass therethrough, while still preventing aqueous liquid (urine) from passing therethrough, which can help improve comfort of the pant for the wearer. Materials for suitable topsheet and backsheet materials are well-known in the art. The materials of the topsheet and backsheet may be joined and bonded together about their peripheries, to form an envelope structure containing the absorbent structure 65, by any suitable bonding mechanism, for example, hot melt adhesive.

FIG. 3 is a schematic, exploded cross-section view showing the depicted absorbent pad assembly components separated from each other. Some adhesive layers are shown in dotted lines, it will be appreciated, however, that the materials depicted may be bonded together to form the pant assembly by any suitable mechanism, for example, by thermal bonding, or by hotmelt adhesive deposited between the respective components to be bonded. For example, the topsheet 60 and backsheet 66 may be bonded together about their perimeters to form an envelope structure that contains the absorbent structure 65. Similarly, the proximal portions 82 of barrier leg cuffs 80 may be bonded to the topsheet or other portion of the assembly by any suitable mechanism such as hotmelt cuff adhesive 69.

The absorbent article of the invention comprises a relatively narrow stabilization element 100. The stabilization element 100 is preferably disposed between the absorbent core 26 and the topsheet 60, but it is not excluded that it may also be placed between the absorbent core 26 and the backsheet 66, or within the absorbent core 26.

Figure 5:
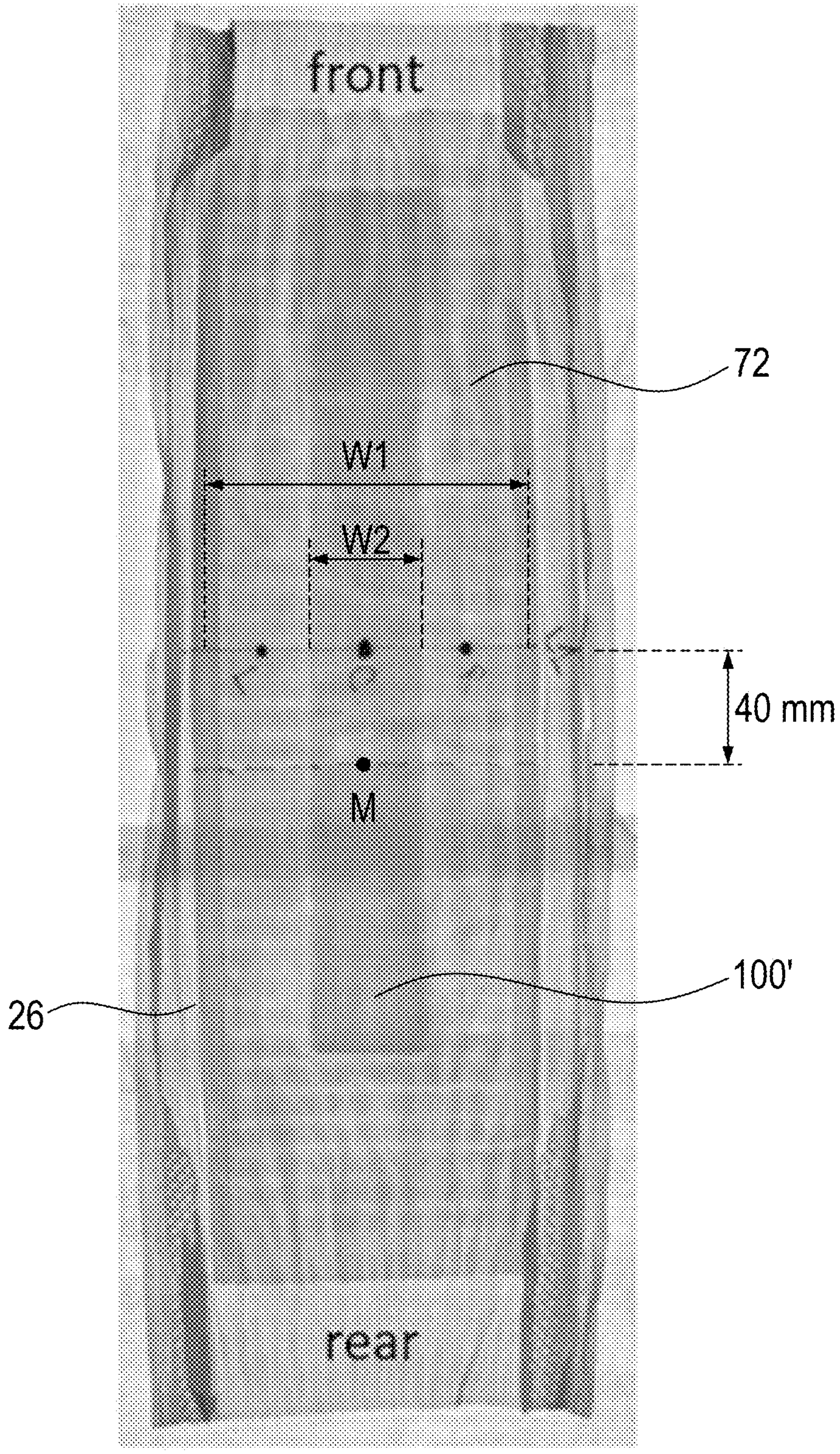
FIG. 5 is a photographic top view of an absorbent pad assembly showing the position of the points C, R and L.
Figure 6:
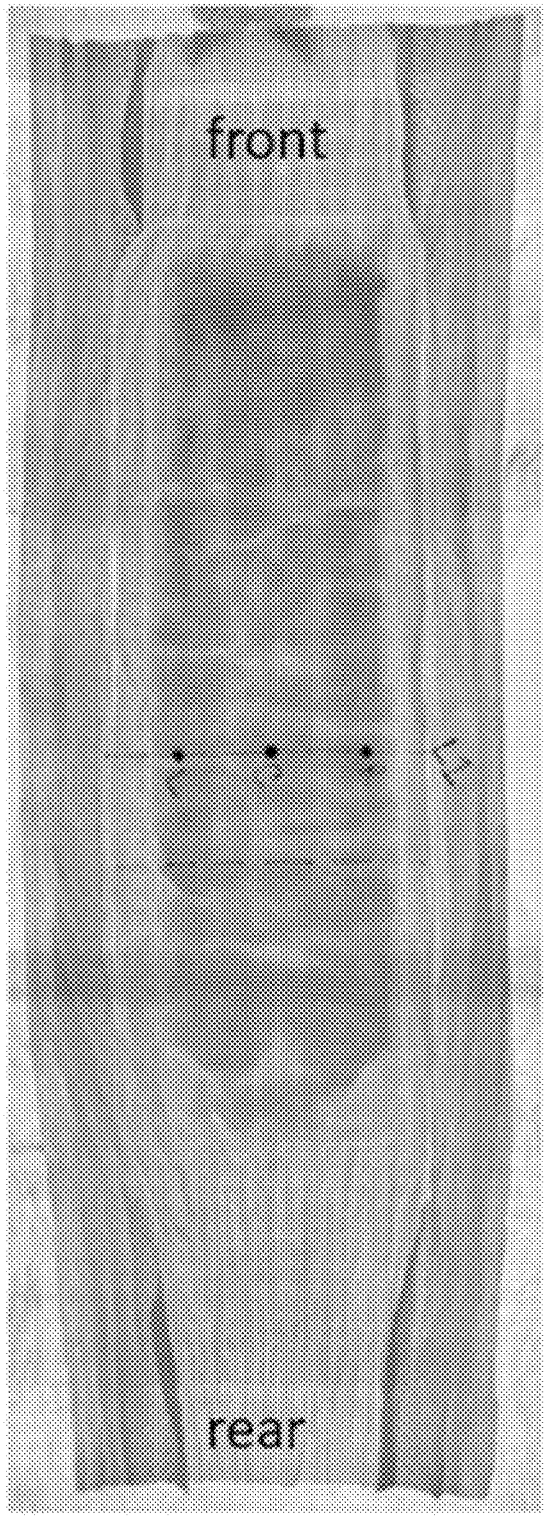
Fig. 6 Prior Art
FIGS. 6 and 7 are photographic top views of prior art absorbent pad assembly.
Figure 7:
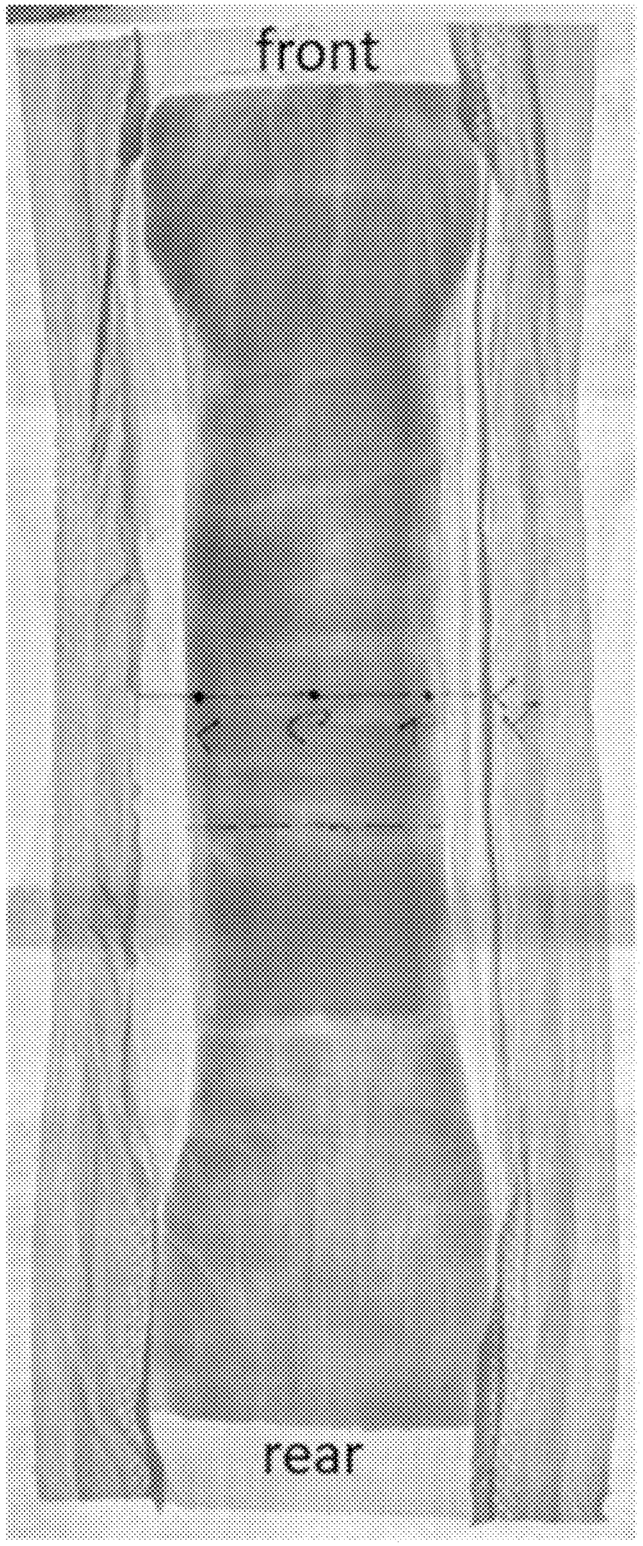
Fig. 7 Prior Art

The absorbent core 26 comprises a layer of absorbent material 72 (herein "absorbent material layer") sandwiched between a core wrap top layer 91 and a core wrap bottom layer 92. The transversal stabilization 100 is relatively narrow relative to the rest of the article in the crotch region. The absorbent material layer 72 has a width W1 and the transversal stabilization element 100 has a width W2, both measured in the transversal direction at the point C disposed about 40 mm towards the front of the article (point C) from the Midpoint M of the article. According to the invention, W2 should be equal to or less than about 50 mm, and preferably W2 is in the range of from about 20 mm to about 50 mm, more particularly from 25 mm to 45 mm, most preferably from about 30 mm to 40 mm. The width W1 of the absorbent material layer 72 of the absorbent core 26 may on the other hand typically have a value ranging from 70 mm to 150 mm. The ratio of W1 divided by W2 may be of least about 1.5 (75/50), in particular in the range of about 2.0 to about 4.0. The width is measured transversally (parallel to the transversal centerline), as illustrated in FIGS. 3-5 and further detailed in the Width and Caliper Measurement Method below.

The benefits of the invention are described further below in the "experimental section" with a more detailed description of the principal components of the invention described below.

Stabilization Element 100

The absorbent article of the invention comprises a narrow stabilization element 100 that can provide resistance against excessive transversal compression in the crotch region of the article. The stabilization element may be disposed between the topsheet and the absorbent core, as illustrated in FIGS. 3-4, however other positioning is possible, for example between the absorbent core and the backsheet.

Various materials may be used for the stabilization element. The stabilization element may comprise or consist of synthetic or cellulosic fibers. The stabilization element may be a fibrous layer comprising unbound or loosely bound hydrophilic fibers, in particular cross-linked cellulose fibers. The stabilization element may also be a nonwoven, such as a spunlace, or an airlaid material. The stabilization element may additionally have fluid acquisition or distribution properties in addition to stabilize the absorbent article.

The stabilization element may for example consist of cross-linked cellulose fibers. The stabilization element may comprise at least 50% by weight, optionally consisting of 100%, of cross-linked cellulosic fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf), however not in the manner of the invention. The cross-linked cellulosic fibers provide higher resilience and therefore higher resistance against the compression in the product packaging or in use conditions, e.g., by the thighs of the wearer.

The stabilization element may also be a mechanically integrated nonwoven. Fiber integration of a nonwoven can occur via any suitable process which entangles staple fibers primarily in a Z-direction (positive or negative). Mechanical integration processes include needlepunching and spunlacing, and do not require chemical or adhesive integration.

Needlepunching involves the mechanical interlocking of fibers of a spunbonded and/or carded web(s). In the needlepunching process, a plurality of barbed needles repeatedly pass in and out of nonwoven web(s) and push fibers of the nonwoven web(s) in a positive and/or negative Z-direction. In contrast, the spunlace process uses high-speed jets of water to cause the interlocking of fibers of a nonwoven web(s). The high-speed jets of water push fibers of the nonwoven web in the positive or negative Z-direction. With the aid of a microscope, needlepunched nonwoven materials comprise a plurality of discrete Z-direction fiber integrations in both MD and CD directions, while spunlace nonwovens generally comprise much more continuous integrations along the MD direction but discrete in the CD direction.

Due to the fiber integration, the integrated nonwoven does not require an adhesive or a latex binder for stability. Additionally, a carded staple fiber nonwoven can be manufactured from an assortment of suitable fiber types that produce the desired performance characteristics. Mechanically integrated stabilization element such as spunlace may comprise a combination of absorbent fibers, stiffening fibers and resilient fibers, as further detailed below (the percentage are disclosed for spunlace but may also apply to other vertically integrated nonwovens).

Any suitable absorbent fibers may be utilized. Some conventional absorbent fibers include cotton, rayon or regenerated cellulose or combinations thereof. In one example, the absorbent fibers may comprise viscose cellulose fibers. The absorbing fibers may comprise staple length fibers. The staple length of the absorbing fibers can be in the range of about 20 mm to about 100 mm, or about 30 mm to about 50 mm or about 35 mm to about 45 mm, specifically reciting all values within these ranges and any ranges created thereby. Overall, the spunlace may comprise from about 20 percent to about 75 percent by weight, or from about 25 percent to about 60 percent by weight, or from about 30 percent to about 50 percent by weight, specifically including any values within these ranges and any ranges created thereby, of absorbent fibers. In one specific example, the spunlace may comprise about 50 percent by weight absorbent fibers.

In addition to absorbent fibers, the spunlace may also comprise stiffening fibers. Stiffening fibers may be utilized to help provide structural integrity to the nonwoven. The stiffening fibers can help increase structural integrity of the nonwoven in a machine direction and in a cross machine direction which can facilitate web manipulation during processing of the nonwoven for incorporation into a disposable absorbent article. Any suitable stiffening fiber may be utilized. Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core-sheath arrangement where the polyethylene is the sheath. As another example, mono-component fibers may be utilized, and the constituent material of the mono-component may comprise polypropylene or polylactic acid (PLA). It is worth noting that these components, e.g., polypropylene and polylactic acid can also be utilized in bi-component fibers as well. The stiffening fibers can be polyethylene terephthalate (PET) fibers, or other suitable non-cellulosic fibers known in the art.

The staple length of the stiffening fibers can be in the range of about 28 mm to about 100 mm, or in the range of about 37 mm to about 50 mm. Some carded staple fiber nonwovens include stiffening fibers with a staple length of about 38 mm to 42 mm. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded staple fiber nonwoven, the stiffening fibers may be fibers made of hollow/spiral PET. Optionally, the stiffening fibers may be spiral-crimped or flat-crimped. The stiffening fibers may have a crimp value of between about 4 and about 12 crimps per inch (cpi), or between about 4 and about 8 cpi, or between about 5 and about 7 cpi, or between about 9 and about 10 cpi. Particular non-limiting examples of stiffening fibers can be obtained from Wellman, Inc. Ireland under the trade names H1311 and T5974. Other examples of suitable stiffening fibers for utilization in the carded staple fiber nonwovens detailed herein are disclosed in U.S. Pat. No. 7,767,598 (Schneider et al.).

Overall, spunlace nonwovens may comprise from about 1 percent to about 50 percent, or from about 10 percent to about 40 percent, or from about 20 percent to about 30 percent of stiffening fibers, specifically reciting all values within these ranges and any ranges created thereby. In one specific example, the nonwoven may comprise about 20 percent by weight stiffening fibers.

As noted previously, the mechanically integrated (e.g., spunlace) nonwoven of the present disclosure may additionally comprise resilient fibers. The resilient fibers help the nonwoven to maintain its permeability and cushion properties. Suitable fibers that may be utilized include in particular hollow fibers, spiral fibers, and/or hollow spiral fibers. For example, the resilient fibers can have a linear density of about 4 dtex to about 12 dtex, from about 6 dtex to about 11 dtex, or from about 8 dtex to about 10 dtex, specifically reciting all values within these ranges and any ranges created thereby. In one specific example, the resilient fibers may comprise a linear density of about 10 dtex hollow spiral polyethylene terephthalate fibers. In another specific example, the resilient fibers may comprise 6.7 dtex round polyethylene terephthalate fibers.

The resilient fibers can be any suitable thermoplastic fiber, such as polypropylene (PP), polyethylene terephthalate, or other suitable thermoplastic fibers known in the art. The staple length of the resilient fibers can be in the range of about 20 mm to about 100 mm, or about 30 mm to about 50 mm or about 35 mm to about 45 mm. The resilient fibers may have a circular cross section with a hollow space in the centre that is spiral crimped. It is preferred that 10-15% of the cross-sectional area are hollow, more preferably 20-30% of the cross-sectional area are hollow. Without wishing to be bound by theory, it is believed that the spiral crimping of fibers is beneficial for their liquid acquisition and distribution behaviour. It is assumed that the spiral crimp increases the void space in an acquisition member formed by such fibers.

Overall, a spunlace as used in the present invention may comprise from about 10 percent to about 50 percent, or from about 13 percent to about 40 percent, or from about 20 percent to about 35 percent, or from about 25 percent to about 30 percent by weight of resilient fibers, specifically reciting all values within these ranges and any ranges created thereby. In one specific example, the spunlace nonwoven of the invention may comprise about 30 percent by weight resilient fibers.

In order to enhance the stabilizing effect of the integration, one or more of these fibers may be crimped prior to integration. For example, where synthetic fibers are utilized, these fibers may be mechanically crimped via intermeshing teeth. And for the absorbent fibers, these fibers may be mechanically crimped and/or may have a chemically induced crimp due to the variable skin thickness formed during creation of the absorbent fibers.

In addition to cross-linked cellulose fibers and mechanically integrated nonwovens such as spunlace as discussed above, the narrow stabilization element may also be constituted by airlaid material comprising fibers which are bonded to form a continuous and homogeneous web. The airlaid fibers typically comprise cellulose fibers optionally mixed with synthetic fibers. Common bonding techniques are latex bonded (LBAL), thermal bonding (TBAL), and multi-bonding (MBAL) combining latex and thermal bonding.

More generally, the stabilization element may typically have an average basis weight of at least 50 g/m$^2$, preferably in the range from about 50 g/m$^2$ to about 400 g/m$^2$, in particular from 80 g/m$^2$ to 240 g/m$^2$. The average basis weight is calculated by dividing the weight of the stabilization element by its surface area. The stabilization element may have a uniform basis weight, as is typically the case for nonwoven material. The stabilization element may also have a basis weight locally varying along the length of the article, for example with higher basis weight at the front and middle of the layer than at its back. This may be in particular when the stabilization element is comprised of loosely bonded fibers, such as cross-linked cellulose fibers. Such a stabilization element may for example be made on-line by depositing the fibers, for example cross-linked cellulosic fibers, on a forming surface within a deposition chamber having varying depth so that the locally deposited basis weight may vary. The deposition chamber may have a forming surface having a series of small holes connected to source of a negative pressure vacuum, so that the suction pulls the fibers in the desired emplacements to form a layer of the desired form and shape. The fibrous layer may be formed or transferred on a carrier sheet, which should thus have at least the same dimension as the fibrous stabilization element. The carrier sheet may for example be the topsheet, another liquid management layer such as a nonwoven acquisition layer 70, or any other layer of the article, for example the core wrap top layer 91.

The stabilization element 100 is typically at least present in the middle of the article, as materialized by the point M defined above. The stabilization element also extends at least on the longitudinal centerline at a distance of at least 40 mm from the transversal centerline towards the front (and preferably also the back of the absorbent article) to a point C. At this point C, the stabilization element extends widthwise no more than 50 mm in the transversal direction. The stabilization element typically has a width in the range of from about 20 mm to about 50 mm as measured at the point C, and preferably has a width in the range of from about 20 mm to about 50 mm also at the point M. Having a narrow width for the stabilization element was found to prevent pressure on the inner legs during walking or other activities while sufficiently wide to reduce wrinkling at least in the crotch region of the absorbent article, both visually and tactilely. The stabilization element 100 may typically have a generally rectangular shape, as this may be the most efficient use of material which are provided in a roll such as a nonwoven. Other shapes are also possible, for example sand-hour or dog bone shape, trapezoidal shapes etc. when the stabilization element comprises airlaid fibers, these can be airlaid in a mold having the desired shape. The stabilization element 100 may have a longitudinal dimension as measured on the longitudinal centerline in the range of from 100 mm to 500 mm. For adult incontinence pants application, the length of the stabilization element may in particular range from 200 mm to 400 mm.

While the stabilization element may be a single layer component for simplicity of construction (this also including integrated layer such as spunlace comprising two or more strata) the stabilization element may be a multi-layer component comprising at least two sub-layers. The sub-layers may be stacked individual layers, or the sub-layers may be formed by folding a layer of material, the folds forming the sub-layers. The sub-layers may be arranged so that the stabilization element has a higher basis weight in a longitudinally-extending central area relative to the lateral areas disposed transversally outwardly of this central area. In this manner, the stabilization element provides increased stabilization in this central area of the article, where it is most needed. This can be obtained by stacking at least two sub-layers with different width. Two vertically adjacent sub-layers forming the stabilization element may be homogeneously attached to another at their interface, or according to an attachment pattern comprising a central longitudinally-extending attachment area but without attachment to lateral non-attachment areas disposed transversally outwardly of the central attachment area. When the stabilization element is made up of two or more layers, each of the layers is 50 mm or less in width. Also, the combined total basis weight of the two or more layers is preferably greater than 50 gsm also the individual layers may have a lower basis weight.

Absorbent Core 26

The absorbent core 26 may be an unitary component comprising an absorbent material layer 72 that provides absorbent capacity to the absorbent article sandwiched between a core wrap bottom layer 92 and a core wrap top layer 91.

The absorbent material layer 72 may comprise or consist of superabsorbent polymer (SAP) particles. SAP are water-insoluble, water-swellable polymers capable of absorbing large quantities of fluids. The term "superabsorbent polymer" refers herein to absorbent materials that can absorb at least 10 times their weight of an aqueous 0.9% saline solution as measured using the Centrifuge Retention Capacity (CRC) test as indicated in EDANA method WSP 241.2.R2 (19). The SAP may in particular have a CRC value of more than 20 g/g, or more than 24 g/g, or of from 20 g/g to 50 g/g, or from 20 g/g to 40 g/g, or 24 g/g to 35 g/g. The SAP may be cross-linked polyacrylates, or other type of polymers as known in the art.

The absorbent material may comprise superabsorbent polymer particles mixed with cellulose fibers (as is known in airfelt cores) or may be free of cellulose fibers (as is known in airfelt-free cores). The absorbent material advantageously comprises a high proportion of SAP. The absorbent material may in particular comprise at least 70%, in particular at least 80%, or at least 90% and up to 100% of SAP by weight of the absorbent material. The resulting absorbent cores with high proportion of SAP typically have a reduced thickness in the dry state compared to conventional absorbent cores that comprise cellulosic fibers as absorbent material. The reduced thickness helps to improve the fit and wearing comfort of the absorbent article. The absorbent material layer in the invention may be free of cellulose fibers. The absorbent core may comprise at least one layer of SAP which is not mixed with of cellulose fibers.

The absorbent material layer 72 may optionally comprise at least one channel-forming area (not represented). Channel-forming area are areas within the absorbent material layer which are intentionally left free of absorbent material, with the possible exception of particles accidentally deposited during core-making. The channel-forming area preferably does not extend to any of the side of the absorbent material layer, and thus is completely surrounded by the absorbent material. The channel-forming area is typically elongated in the longitudinal direction, having a longitudinal length of from 20% to 80%, or from 20% to 70%, or from 30% to 60%, of the longitudinal length of the layer of absorbent material (longitudinal length means the length as measured projected on the longitudinal centerline). The absorbent core may comprise a pair of channel-forming areas disposed symmetrically on each side of the longitudinal centerline 2, wherein these channel-forming areas may be straight, curved, or combinations thereof. Such a pair of channel-forming areas may be disconnected, but alternatively the channel-forming areas may also be connected, for example at one or both their extremities to form a U or O shape. Examples of channel-forming areas are disclosed in further details in WO2012170778A1, WO2012170781 (Kreuzer et al.).

The absorbent material layer 72 may advantageously comprise a high proportion of SAP. Various absorbent core designs comprising high proportion of SAP as absorbent material have been proposed, see for example in U.S. Pat. No. 5,599,335 (Goldman), EP1,447,066 (Busam), WO95/11652 (Tanzer), US2008/0312622A1 (Hundorf), WO2012/052172 (Van Malderen). In particular, the SAP printing technology as disclosed in US2006/024433 (Blessing), US2008/0312617 and US2010/0051166A1 (both to Hundorf et al.) may be used.

The absorbent material layer is typically deposited on a substrate which is part of the absorbent core, such as the core wrap bottom layer 92 or core wrap top layer 91. In the SAP-printing process as described in US2008/312,622A1 (Hundorf), a continuous layer of SAP is obtained by depositing SAP on each of the core wrap layers in a pattern having absorbent material land areas separated by absorbent material-free junction areas. The absorbent material land areas of the first layer correspond substantially to the absorbent material-free junction areas of the second layer and vice versa, so that a continuous layer of SAP is obtained when the two discontinuous layers are combined.

The total amount of SAP present in the absorbent core is adapted to the need of the expected wearer of the article. For adult incontinence products, the amount of SAP in the core may be for example comprised from about 2 g to 50 g, in particular from 5 g to 40 g, and from 10 g to 20 g e.g., for typical adult incontinence articles. The average SAP basis weight within the absorbent core may be of at least 50, 100, 200, 300, 400, 500 g/m2 or more, and typically in the range from 200 g/m$^2$ to 600 g/m$^2$, in particular from 400 g/m$^2$ to 525 g/m$^2$, as calculated by dividing the total amount of SAP divided by the surface area of the absorbent core.

Core Wrap Layers 91, 92

The absorbent core 26 typically comprises a core wrap. The core wrap may comprise a core wrap top layer 91 and a core wrap bottom layer 92 sandwiching the absorbent material layer 72. The top and bottom core wrap layers may be comprised of any material capable of containing and providing a support for the absorbent material. The core wrap may be made of a single, continuous nonwoven web, which is wrapped around the layer of absorbent material. The core wrap layers may alternatively be each made of discrete web of material as illustrated in FIG. 3 and FIG. 4. These discrete layers may be joined for example in a c-wrap configuration as illustrated in these Figures. Having different materials for the top layer and the bottom layer can be used to provide different properties to the top side and bottom side of the core wrap, in particular the top layer 91 may be more hydrophilic than the bottom layer 92.

The basis weight of the core wrap layers is typically homogeneous throughout the length and width of the core wrap layer (i.e., for each layer is homogeneous in the longitudinal and transversal direction). The value of the basis weight of a material is typically provided by the supplier, and if not can be calculated by dividing the weight of the layer by its surface area. Typical core wrap layers are typically low basis weight nonwoven (typically less than 20 g/m$^2$, in particular in the range of 8 g/m$^2$ to 14 g/m$^2$). The top and bottom core wrap layers 91,92 may comprise or consist of a nonwoven layer. The nonwoven layer may be any type of conventional nonwovens. SMS nonwoven (Spunbond-Meltblown-Spunbond laminate) are typically used in the art. Carded nonwovens (made of staple fibers) for example are suitable. Carded nonwovens may be hydroentangled (spunlace), calendar bonded or air-through bonded, as is known in the art. The nonwoven layer may also be a spunbond or meltblown nonwoven web (made of continuous fibers) or a nonwoven with spunbond and meltblown layers (e.g., an SMS, SMMS, SMSS or the like).

The absorbent article 10 may optionally include an acquisition layer 70 disposed directly under the topsheet in order to provide fast acquisition of the fluid away and from the topsheet, as illustrated in FIG. 3. In case of a pant comprising an absorbent pad assembly 50, the acquisition layer 70 is part of the absorbent pad assembly. Any typical acquisition layers known in the art may be used, for example a surfactant treated nonwoven acquisition layer. Typical basis weight for such an acquisition layer range from 20 g/m$^2$ to 70 g/m$^2$, in particular from 30 g/m$^2$ to 60 g/m$^2$. The acquisition layer may be a latex-bonded nonwoven, or an air-through bonded nonwoven, or any other conventional acquisition layer as is known in the art.

Such an acquisition layer 70 may provide sufficient fluid handling properties so that a conventional, low basis weight, core wrap material may be used for the core wrap top layer 91. The core wrap top layer 91 may thus be selected from a material having relatively high fluid acquisition properties. Typical low basis weight core wrap top layer nonwovens may comprise a hydrophilic agent, especially if the core wrap top layer comprises or consists of synthetic fibers that are inherently hydrophobic. Any conventional hydrophilic treatments may be used to provide the hydrophilic agent. Typically, a web such as a nonwoven can be externally coated by a surfactant directly or via an oil/emulsion. Alternatively, hydrophilic melt additives can be added in the polymer melt used to make the fibers, as is known in the art. Hydrophilic melt additives are amphiphilic molecules having a hydrophilic head and a hydrophobic tail. The hydrophilic head is oriented towards the surface of the adhesive, thus providing for the hydrophilic character of the adhesive, while the hydrophobic head remains in the polymer matrix.

Alternatively, the absorbent articles of the invention may be free of such an acquisition layer, as illustrated in FIG. 4. This may be particularly the case when the stabilization element 100 and/or the core wrap top layer 91 already at least partially provide for fluid acquisition or distribution properties. This may be especially the case for light adult incontinence article, where each gush of urine to be handled is relatively less than for baby diapers for example.

Thus, in a second embodiment as illustrated in FIG. 4, despite the reduced width of the stabilization element, the acquisition layer 70 may be eliminated or reduced if the stabilization element 100' and/or the core wrap top layer 91' have sufficient liquid handling properties to compensate for the reduced width of the stabilization element 100. In order for the core wrap top layer 91' to serve as a temporary storage layer for urine to be absorbed by the absorbent material layer 72, the basis weight of the core wrap top layer may be relatively high relative to typical prior art core design. In particular the basis weight of the core wrap top layer 91' may be in the range of from about 40 g/m$^2$ to about 200 g/m$^2$, or from 60 g/m$^2$ to 180 g/m$^2$, or from 80 g/m$^2$ to 160 g/m$^2$. Air-through bonded nonwoven generally have high loft, meaning they have a porous structure to provide void volume for absorbing and temporarily holding liquid. At the same time, they provide softness and do not have an excessively high bending stiffness. Likewise spunlace nonwovens, which are hydroentangled, may be advantageously used as core wrap top layer 91'. Spunlace materials as disclosed above for the stabilization element 100 may also be used as a core wrap top layer 91'. When the absorbent article does not comprise a separate acquisition layer 70, the core wrap top layer 91' may thus advantageously by material having good acquisition properties, such as a spunlace.

The core wrap top layer 91' may comprise staple fibers. Staple fibers are preferably air-through bonded or hydroentangled (spunlace). In addition to hydroentanglement or air-through bonding, the nonwoven web of staple fibers may or may not have undergone some localized bonding with heat and/or pressure (e.g., point bonding/calendar bonding), introducing localized bond regions where the fibers are fused to each other.

Through-air bonding (interchangeably used with the term "air-through bonding") means a process of bonding staple fibers or continuous fibers by forcing air through the nonwoven web, wherein the air is sufficiently hot to melt (or at least partly melt, or melt to a state where the fiber surface becomes sufficiently tacky) the polymer of a fiber or, if the fibers are multicomponent fibers, wherein the air is sufficiently hot to melt (or at least partly melt, or melt to a state where the fiber surface becomes sufficiently tacky) one of the polymers of which the fibers of the nonwoven web are made. The air velocity is typically between 30 and 90 meter per minute and the dwell time may be as long as 6 seconds. The melting and re-solidification of the polymer provide the bonding between different fibers. The hot air melts the staple or continuous fiber, or, for multicomponent fibers, the lower melting polymer component of the fiber and thereby forms bonds between the staple fibers to consolidate and integrate the layer of staple fibers into a web.

The core wrap top layer 91' may comprise multicomponent fibers. The multicomponent fibers may be bicomponent fibers, such as core-sheath or side-by-side bicomponent fibers. The core wrap top layer 91' may also comprise monocomponent fibers. The fibers of the nonwoven may comprise at least 30 weight-%, or at least 40 weight-%, or at least 50 weight-%, or at least 70 weight-%, or at least 90 weight-% or 100 weight-% of monocomponent fibers based on the total weight of the nonwoven. The nonwoven web comprised by or forming the core wrap top layer may comprise a mixture of monocomponent fiber and multicomponent fibers.

In general, the fiber dtex (linked to the fiber's diameter) is directly impacting the pore size of the material and therefore especially the capillary pressure and permeability/strike-in and strike-through of the material. At a given basis weight, the lower the dtex, the lower the permeability and higher the capillary pressure. The core wrap top layer 91,91' may comprise fibers having at least 50%, or at least 70%, or at least 80% and up to 100% by weight of fibers having a denier below 10 dtex.

In general, the core wrap top and bottom layers are preferably bonded longitudinally by one or more longitudinal core wrap bond(s) 93 to prevent the absorbent material from escaping sideways from the absorbent core. The core wrap layers may also be optionally bonded transversally at the front and the back of the absorbent core by one or more transversal core wrap bonds. The core wrap layers may be bonded face to face, at least longitudinally as represented or in a C-wrap configuration. The core wrap bottom layer 92 may be wider than the core wrap top layer 91, so that flaps formed by core wrap bottom layer can be folded around the absorbent material and attached to the core wrap layer as illustrated in FIGS. 3-4. While the inverse configuration is possible, when the core wrap top layer is of a higher basis weight than the bottom core wrap layer, as illustrated in FIG. 4, it is advantageous to reduce usage of the higher basis weight material by C-wrapping the core wrap bottom layer 92, in order to reduce usage of the more expensive top core wrap material layer 91'.

The core wrap top layer 91,91' and the core wrap bottom layer 92 typically at least partially or fully enclose the absorbent material layer 72, providing for dry and wet immobilization of the absorbent material.

The absorbent core may comprise one or more glue layers, in particular an auxiliary glue 94 applied between the internal surface of one or both of the core wrap layers and the SAP layer to adhesively immobilize the SAP within the core wrap. Additionally, the SAP layer may at least partially be immobilized on the core wrap top layer and/or on the core wrap bottom layer by a thermoplastic fibrous network applied on layer of the SAP. These adhesives are not represented in the Figures for simplicity.

The core wrap top layer 91 and core wrap bottom layer 92 are preferably bonded to each other through at least a portion of the length of the core channel-forming area(s) if these are present (not represented). This bond provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO2012/170798A1 (Jackels et al.), EP2,905,000 (Jackels et al.) and EP2,905,001 (Armstrong-Ostle et al.).

Other bonding such as thermo bonding, mechanical bonding, ultrasonic bonding can also be used as additional bonding or as an alternative bonding. For example, an adhesive bonding may be reinforced by a thermo bonding, mechanical bonding or ultra-sonic bonding. Such thermo, mechanical or ultrasonic bonding can be applied on the channels through the external sides of the core wrap layers.

Other Components

The absorbent pad assembly 50 typically includes a pair of longitudinally-extending barrier leg cuffs 80, each cuff disposed on a longitudinal side of the absorbent pad assembly. The barrier leg cuffs 80 comprise each a proximal portion 82 attached to the absorbent pad assembly, for example via adhesive 69, and a respective free edge 84 that can extend away from the assembly and toward the wearer. Barrier leg cuffs advantageously comprise an elastic member 86 disposed along the free edge 84. When the absorbent pad assembly curves about the wearer's body through the crotch region, the free edges 84 are pulled longitudinally taut by barrier cuff edge elastic members 86 as is known in the art. Barrier cuff edge elastic members 86 may be incorporated into the cuff structures while in a pre-strained condition, which will cause the free edges to be in longitudinal tension and tend to gather to cause the edges to extend away from the assembly and conform to the wearer's body contours when the pant is worn.

The barrier leg cuffs may be formed of an effectively liquid impermeable material, such as a film material or a breathable but effectively liquid impermeable nonwoven web material, and may serve to contain discharges of urine within the pant prior to its absorption by the absorbent structure. The absorbent article may optionally also include outer cuffs, also called gasketing cuffs, provided by elastic strands disposed on the outer longitudinal edges of the absorbent assembly while in a pre-strained condition (this dual cuff construction is not represented in the Figures). The outer cuffs can cause the longitudinal left and right edges of the assembly to gather about the wearer's legs through the crotch region, furthering the containment function and enhancing fit. Longitudinal edge elastic members may be disposed between the materials of the barrier cuffs 80 and topsheet 60, alternatively they may be disposed between the topsheet and backsheet, or outside of the outward-facing side of the backsheet. However, barrier outer cuffs typically increase the width of the absorbent assembly. In the present invention, it was found that barrier outer cuffs may be dispensed of. The article of the invention may thus be free of barrier outer cuffs. In particular the absorbent assembly may comprise barrier leg cuffs 80 (inner cuffs) as described above, but may be free of barrier outer cuffs.

The barrier cuff elastic members 86 are typically elastic strands, which may be of the same or different material as that of elastic strands 40 in the panels 20, 30. One, two or more of such elastic strands 86 may be disposed in a fold of the cuff material. Barrier cuffs and associated longitudinal edge structures and elastic members may also be formed of materials and configured as described in any of, for example, U.S. Pat. No. 8,939,957; US2016/270978; US2016/270971; US2016/270980; US2016/270985; US2016/270983; US2016/270979; US2016/270975; US2016/270981, and US2016/270973.

Relations Between the Layers and Process for Making

The individual components may be converted into an absorbent article according to the processes known in the art. Typically, adjacent layers will be joined together using conventional bonding method such as adhesive coating via slot coating or spraying on the whole or part of the surface of the layer, or thermo-bonding, or pressure bonding or combinations thereof. All bonding between components is for clarity and readability not represented in the Figures. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. For example, as illustrated in FIG. 3, construction adhesives 96, 97 may be applied between the topsheet 60 and an acquisition layer 70, and between the acquisition layer 70 and the stabilization element 100 respectively, for example by slot coating. In the absence of a separate acquisition layer 70 between the topsheet and the absorbent core, as illustrated on FIG. 4, the stabilization element 100' may be directly attached to the topsheet by a slot coated adhesive 98. The stabilization element 100, 100' may also be adhesively attached to the core wrap top layer 91 by an adhesive 99. Typically an adhesive 95 is applied on the inner-facing side of the backsheet 66 e.g. by a spiral coating to solidarize the components (absorbent core, topsheet, barrier leg cuffs) directly with the backsheet.

Packages

A plurality of articles according to the invention will be typically packaged together for transport and sale. The articles may be folded and packaged as is known in the art. The package may be for example a plastic bag or a cardboard box. Disposable absorbent pants may typically be bi-folded along the transversal centerline and the side panels folded inwardly before being packaged. The absorbent articles may be packed under compression so as to reduce the size of the packages, while still providing an adequate number of absorbent articles per package. By packaging the absorbent articles under compression, caregivers can easily handle and store the packages, while also providing distribution and inventory savings to manufacturers owing to the size of the packages. Primary packages may typically contain from 8 to 40 articles, but other counts are of course possible, for example individually packaged articles may be also provided.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in US2019/0192723, published on Jun. 27, 2019.

EXAMPLES

First Examples

Example 1 (Code GD) is an adult incontinence pant according to the invention and as generally illustrated in the FIGS. 1-3. Dimensions are indicated as Width×Length format. This example 1 comprised a 90 mm×305 mm latex-bonded acquisition layer (70), and a 40 mm×305 mm stabilization element (100) consisting of cross-linked cellulose fibers and having a basis weight of 144 g/m$^2$. The core was an airfelt-free absorbent core containing 16.3 g of SAP (absorbent layer dimensions 120 mm×400 mm). The core wrap top layer was a 130 mm wide, 55 g/m$^2$ spunlace. The spunlace had a homogenous composition comprising, by weight, 20% Viscose 1.3 dtex, 30% PET Hollow Spiral 10 dtex, and 50% PE/PET (Sheath/Core) 2.2 dtex. The core wrap bottom layer was a 165 mm wide, 10 g/m$^2$ SMS. The overall core bag dimensions were 120 mm×430 mm.

Example 2 (comparative, Code JD) was Always® Discreet Underwear Max S/M having a 55 mm wide cross-linked cellulose layer.

Example 3 (comparative, Code H) was Depend® Fit Flex Maxi Small.

Caliper measurements of the articles listed above were executed according to the Width and Caliper Measurement Method disclosed herein, and are reported below in Table 1.

TABLE 1

Caliper measurements

| | | Thickness (mm) | | | | |
|---|---|---|---|---|---|---|
| Product | N | C3 (Position "L") | C1 (Position "C") | C2 (Position "R") | Avg. caliper (C2 + C3)/2 | Caliper Ratio C1/(C2 + C3) |
| Code GD | 10 | 3.06 | 4.26 | 3.13 | 3.10 | 0.69 |
| Code JD | 10 | 9.14 | 8.27 | 7.13 | 8.13 | 0.51 |
| Code H | 10 | 8.72 | 9.61 | 8.31 | 8.52 | 0.57 |

Panelists under CDA were asked to use 10 pants of each leg. The pants were randomized via rotation generator. Each panelist completed a diary for each product, weighed used product and completed an online questionnaire for each code. Results are summarized in Table 2-3 below.

TABLE 2

| Diary Data | | | |
|---|---|---|---|
| | GD | JD | H |
| Did the product feel bunched between the legs during wear? | 30% | 36% | 35% |
| Did the product sag at the crotch during wear? | 16% | 18% | 33% |
| Did the product conform to your crotch during wear? | 78% | 76% | 70% |

TABLE 3

| Questionnaire Data<br>Scale 1-5 (poor, fair, good, very good, excellent) | | | |
|---|---|---|---|
| | GD | JD | H |
| Doesn't feel bulky between my legs | 3.4 | 3.1 | 3.3 |
| Comfort between legs | 3.4 | 3.0 | 3.3 |
| Doesn't bunch between the legs | 3.5 | 3.1 | 3.2 |
| I don't notice I am wearing it | 3.5 | 3.1 | 3.2 |

From the diaries, it was found that the reducing the basis weight and width of the cross-linked cellulose layer of the invention example 1 did not negatively impact leakage performance vs. the currently marketed control product (example 2, code JD).

In conclusion, the inventive and current products had significantly less sagging at the crotch and were better conforming at crotch vs. the control products. The inventive product was rated significantly better than the control products for bunching between the legs.

Second Examples

Example 4 (Code T) was a hand-made absorbent pant generally as shown in FIG. 4. The absorbent core (26) was an airfelt-free absorbent core comprising a 40 g/m$^2$ spunlace core wrap top layer.

The stabilization element (100) was a 135 g/m$^2$ spunlace, 40 mm wide comprising two integrated strata:

Layer 1 (Top Stratum):

50% PET 10 dtex Hollow Spiral

50% PE/PET (Sheath/Core) 5.8 dtex

Layer 2 (Bottom Stratum):

50% Viscose 1.3 dtex

50% PE/PET (Sheath/Core) 5.8 dtex

No other acquisition or distribution layer were used for this example. The chassis was a single cuff chassis (without outer barrier cuffs).

Example 5 (code L) was of generally the same construction as Example 4 with the difference that a 90 mm wide spunlace was used instead of the narrow 40 mm stabilization element.

Example 6 (Code C) was Always® Discreet, a marketed adult incontinence article having an airfelt core, a dual acquisition-distribution layer (consisting of a 70 mm wide, 43 g/m$^2$ acquisition layer and a 200 g/m$^2$ cross-linked cellulose layer), and dual cuff system. This is the same product as code JD used in the First examples above.

The differences between the products tested in this series are summarized in the Table below:

TABLE 4

| test product description | | | | | | | | | |
|---|---|---|---|---|---|---|---|---|---|
| Code | Acquisition layer | Stabilization element | Absorbent material | Core Bag Length | Core Bag Width | Absorbent layer Width | Core Wrap Top Layer | Channels | Cuff |
| T | — | 40 mm wide, 135 gsm spunlace | Airfelt free | 430 mm | 120 | 110 | 40 gsm high density Spunlace | Yes | single |
| L | — | 90 mm wide, 135 gsm spunlace | Airfelt free | 430 mm | 120 | 110 | 165 mm wide, 10 gsm SMS | Yes | single |
| C | 70 mm wide, 43 gsm resin bonded nonwoven | 55 mm wide, 200 gsm Cross-linked cellulose | Airfelt | 430 mm | 120 | 110 | 146 mm wide, 10 gsm SMS | — | dual |

Calipers measurements of the articles listed in the examples above were executed according to the Width and Caliper Measurement Method disclosed herein are reported below.

TABLE 5

| Caliper Measurements | | | | | | |
|---|---|---|---|---|---|---|
| | | Thickness (mm) | | | | |
| Product | N | C3 (Position "L") | C1 (Position "C") | C2 (Position "R") | Avg. caliper (C2 + C3)/2 | Caliper Ratio C1/(C2 + C3) |
| Code T | 10 | 2.61 | 3.99 | 2.35 | 2.48 | 0.81 |
| Code L | 10 | 4.04 | 4.17 | 3.99 | 4.01 | 0.52 |
| Code C | 10 | 7.52 | 7.57 | 8.07 | 7.80 | 0.49 |

45 panelists under CDA used 9 products of each of the three codes. The product order was randomized as equally as possible within the six rotation combinations across the panelists. Panelists completed a diary for each product and completed an online questionnaire after each code. The results are summarized in Tables 6-7 below.

TABLE 6

| questionnaire data Scale 1-5 (poor, fair, good, very good, excellent) | | | |
|---|---|---|---|
| | T | L | C |
| Doesn't feel bulky between my legs | 3.6 | 3.1 | 2.9 |
| Comfort between legs | 3.6 | 3.3 | 3.1 |
| Doesn't bunch between the legs | 3.5 | 3.1 | 2.9 |
| I don't notice I am wearing it | 3.5 | 3.2 | 3.1 |

TABLE 7

| diary data (% Yes answer) | | | |
|---|---|---|---|
| | T | L | C |
| Did the product feel bunched between the legs during wear? | 22% | 35% | 46% |
| Did the product sag at the crotch during wear? | 24% | 31% | 33% |
| Did the product conform to your crotch during wear? | 73% | 72% | 71% |

Code T with narrow stabilization element showed meaningful advantages in Comfort, Discretion and Fit related to questions Code L and Code C (Control). Code L showed advantages vs. Control in these same areas but to a lesser degree.

Third Examples

Example 7 (code S) is an adult incontinence pant according to the invention as generally illustrated in FIGS. 1-3. This example comprised as acquisition layer (70) a 110 gsm, 90 mm×325 mm dual strata spunlace. The top strata of the 110 gsm spunlace was about 36 gsm and had the following composition (by weight):

30% 1.3 dtex CV

30% 4.4 dtex PET/CoPET

40% 10 dtex PET HS

The bottom strata of the 110 gsm spunlace was about 74 gsm and had following composition (by weight):

80% 1.3 dtex CV

20% 10 dtex PET HS

Example 7 further comprised as stabilization element (100) a 135 gsm, 40 mm×325 mm strip mosaic MBAL (multi bonded airlaid). The core wrap was comprised of two 10 g/m$^2$ SMS nonwoven, defining overall 120 mm×480 mm core wrap. The absorbent core was an airfelt-free core adhesively immobilized and comprising 16.3 g of SAP.

Comparative example 8 (code L) was marketed Always® Discreet Boutique Underwear Max S/M Mauve. The topsheet and absorbent core had the same construction as example 7, however this comparative article comprised outer leg cuffs (OLC) while the inventive example 2 comprised no outer leg cuffs.

Forty panelists under CDA were given 5 products of each leg to use in place of their normal product. Panelists were asked to complete a diary and weigh used product after each product use and to complete an online questionnaire after each code. The results of the questionnaire and the diary are indicated in the Table 8 and Table 9 below.

TABLE 8

| Questionnaire Data Scale 1-5 (poor, fair, good, very good, excellent) | | |
|---|---|---|
| | S | L |
| Does not feel bulky between my legs | 3.6 | 3.0 |
| Comfort between legs | 3.4 | 3.0 |
| Doesn't bunch between the legs | 3.5 | 2.8 |
| I don't notice I am wearing it | 3.7 | 3.1 |

TABLE 9

| Diary Data (% Yes answer) | | |
|---|---|---|
| | S | L |
| Did the product feel bunched between the legs during wear? | 24% | 39% |
| Did the product sag at the crotch during wear? | 19% | 38% |
| Did the product conform to your crotch during wear? | 73% | 64% |

The stabilization element (135 gsm Mosaic MBAL in this execution) delivered strong real and perceived protection as well as fit perception. The single cuff chassis consisting of the barrier leg cuffs (inner cuffs) appeared to be even more impactful in the thin/flexible core designs of the invention. Crotch and leg fit metrics were significantly better with single cuff chassis.

Commercial Articles Caliper Measurements

Calipers measurements of commercial products were performed according to the Width and Caliper Measurement Method disclosed below. The results are reported in Table 10 below.

TABLE 10

| | Thickness (mm) | | | | Caliper |
|---|---|---|---|---|---|
| Product Tradename, Size (Lot Code) | C3 (Position "L") | C1 (Position "C") | C2 (Position "R") | Avg. caliper (C2 + C3)/2 | Ratio C1/ (C2 + C3) |
| Always ® Discreet S/M (1301478600 81 3020730) | 8.48 | 7.21 | 8.07 | 8.27 | 0.44 |
| Always ® Discreet Boutique S/M (1256478600 81 2561655) | 6.82 | 6.37 | 7.10 | 6.96 | 0.46 |
| Depend Silhouette M/Max (XM1250031 12:55) | 7.01 | 7.53 | 6.97 | 6.99 | 0.54 |

TABLE 10-continued

| | Thickness (mm) | | | | Caliper |
|---|---|---|---|---|---|
| Product Tradename, Size (Lot Code) | C3 (Position "L") | C1 (Position "C") | C2 (Position "R") | Avg. caliper (C2 + C3)/2 | Ratio C1/ (C2 + C3) |
| Depend ® Fit Flex Underwear M/Max (LF1 294 14 X 00:10) | 5.25 | 5.52 | 4.97 | 5.11 | 0.54 |
| Tena ® Intimates Overnight L/Overnight (0272B 1000:08) | 9.57 | 9.27 | 12.15 | 10.86 | 0.43 |
| Tena ® Lady Pants Discreet L (NL 20160823) | 7.42 | 7.58 | 6.79 | 7.10 | 0.53 |

Test Methods

Width and Caliper Measurement Method

Equipment:

- Ono-Sokki GS-503 linear caliper with Ono-Sokki digital gauge DG-3610 or equivalent.
- Flat pressure foot with a diameter of 10.1 mm.
- With no additional mass added to the mechanism, the pressure exerted is equal to 0.45 psi (3.103 kPa).

Sample Preparation and Width Measurement:

- 10 replicates per product variant are prepared and measured as per the procedure below.
- For pant products, the side seams (13) are cut open.
- The front and rear edges (11, 12) of the product are noted as well as the location of any fold lines (typically a fold line may be present along the transversal centerline (4) as the products are typically folded in their middle for packaging).
- The front edge (11) of the product is secured with tape to a benchtop. The rear edge (12) of the product is secured with tape to the benchtop after it is stretched in the longitudinal direction until it lies flat and taut.
- The length of the product is measured along the longitudinal centerline from the middle of front edge of the product to the middle of the rear longitudinal edge of the product.
- The longitudinal midpoint (M) is marked on the body facing (topsheet) side on the longitudinal centerline of the product at a distance equal to half the product length, measured from the front edge (12) of the product.
- The region of the article extending from the longitudinal midpoint M and extending 60 mm toward the front waist edge is then inspected. If a transversal line 40 mm forward of the transversal centerline can be drawn free from residual of folds and winkles, such a line is drawn and defined as L1. If a line at 40 mm would significantly overlap with residua of folds and wrinkles, the region extending 60 mm forward of the longitudinal midpoint (M) is further inspected, and a line L1 is drawn in this region so as to minimize overlap with any residual folds and wrinkles. If there are multiple possible positions for L1 that would equally minimize overlap with residual folds and wrinkles, the position nearest to 40 mm forward of the longitudinal midpoint (M) is chosen. For products which do not have a differentiated front edge and back edge (e.g. because they are symmetrical relative to their transversal centerline), the measurements are made twice for each sample in each direction as indicated previously and then the values averaged.
- The transversal midpoint "C" is marked on the line L1 placed in the center widthwise of the absorbent material layer (72). The point C is generally aligned with the longitudinal centerline, however due to normal tracking uncertainty, the point C may be shifted left or right of the centerline by a few mm. Therefore, the point C is aligned with the center of the absorbent material layer (72) on the line L1. The point C is a location where the central article thickness will be measured.
- Along line L1, two additional marks ("R" and "L") are made on the body-facing (topsheet) side of the product. Mark "R" is drawn at a distance that is 30 mm away from the transversal midpoint C) in a direction towards the right lateral edge of the product. Mark "L" is drawn at a distance that is 30 mm away from the lateral midpoint C in a direction towards the left lateral edge of the product. To note, "right" and "left" sides are determined with respect to body position when the product is worn. Marks "R" and "L" are the locations where the right and left pad thickness will be measured.
- At line L1, the width W2 of the stabilization element (100) is measured as the distance from one lateral edge to the other lateral edge and recorded to the nearest 0.1 mm. This width is more easily measured using a light box (see FIG. 5) where the absorbent material layer (72) can be more effectively distinguished from the other components of the article such as the topsheet or the core wrap.
- At line L1, the width W1 of the absorbent material layer (72) is measured as the distance from one lateral edge to the other lateral edge of the absorbent material layer, and recorded to the nearest 0.1 mm. If an acquisition layer (70) is present, the width of the acquisition layer may also be recorded in a similar manner.
- The tape is removed from the ends of the product to release it from the benchtop.
- The front and back panels (20, 30) and leg elastics (86) are trimmed away from the core insert/core bag using scissors, using care to avoid cutting into any portion of the core insert/core bag.

Caliper Procedure:

- Center location "C" beneath the pressure foot and slowly lower the foot until it makes contact with the topsheet side of the product.
- After the foot has been in contact with the product for 30 seconds, record the thickness to the nearest 0.01 mm making note of the test location.
- In like fashion, repeat for locations "R" and "L".
- Repeat the entire procedure for all 10 replicate test products.

Results:

- The reported value at each test location is the arithmetic mean of the ten individually recorded measurements for the Width W1 and Width W2 to the nearest 0.1 mm and for Central Pad Thickness (C1), Right Pad Thickness (C2) and Left Pad Thickness (C3) to the nearest 0.01 mm.

Misc

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a longitudinal centerline extending in a longitudinal direction and bisecting the absorbent article in a right half and a left half, a transversal centerline extending in a transversal direction orthogonal to the longitudinal direction and bisecting the absorbent article in a front half and back half, wherein the absorbent article comprises:
   - a liquid permeable topsheet;
   - a liquid impermeable backsheet;
   - an absorbent core comprising an absorbent material layer; and
   - a stabilization element;
   - wherein the stabilization element and the absorbent core are disposed between the topsheet and the backsheet;
   - wherein the stabilization element and the absorbent core are superposed at least at a point C disposed at a distance of about 40 mm from the transversal centerline towards the front of the article and transversally aligned on the absorbent material layer, and
   - wherein the stabilization element has a width (W2) of 50 mm or less as measured at the point C according to the Width And Caliper Measurement Method described herein.

2. The absorbent article according to claim 1, wherein the width (W2) of the stabilization element is in the range of from 20 mm to 50 mm.

3. The absorbent article according to claim 1, wherein the absorbent core extends at least transversally to a point R and to a point L disposed respectively 30 mm right and left in the transversal direction of the point C,
   - whereas the stabilization element does not extend transversally to at least at one of point R and point L,
   - wherein the absorbent article has a first caliper C1 at the point C, and wherein the absorbent article has a second caliper C2 at point R and a third caliper C3 at point L, and wherein the caliper ratio C1/(C2+C3) is at least 0.6, the calipers being measured according to the Width And Caliper Measurement Method disclosed herein.

4. The absorbent article according to claim 3, wherein the caliper C1 is less than 5.0 mm and the average value (C2+C3)/2 is less than 4.5 mm.

5. The absorbent article according to claim 1, wherein the stabilization element has an average basis weight of at least 50 $g/m^2$.

6. The absorbent article according to claim 1, wherein the stabilization element comprises a material selected from:
   - cross-linked cellulose fibers; or
   - a nonwoven, in particular a spunlace; or
   - an airlaid material.

7. The absorbent article according to claim 1, wherein the stabilization element is disposed between the topsheet and the absorbent core.

8. The absorbent article according to claim 1, wherein the absorbent article further comprising an acquisition layer between the topsheet and the stabilization element, wherein the acquisition layer has a basis weight in the range of from 20 $g/m^2$ to 70 $g/m^2$ and the acquisition layer has a width greater than 50 mm at the point C, as measured according to the Width And Caliper Measurement Method described herein.

9. The absorbent article according to claim 1, wherein the absorbent core comprises a core wrap, wherein the core wrap has a top layer and a bottom layer, and the absorbent material layer is disposed between the core wrap top layer and a core wrap bottom layer, and wherein the core wrap top layer and core wrap bottom layer are discrete layers which are longitudinally bonded by one or more longitudinal core wrap bond(s).

10. The absorbent article according to claim 1, wherein a width (W1) of the absorbent material layer as measured according to the Width and Caliper Measurement Method described herein is in the range of from 70 mm to 150 mm, and a ratio of W1 divided by W2 is at least 1.5.

11. The absorbent article according to claim 1, wherein the absorbent core comprises at least 10 g of superabsorbent polymers.

12. The absorbent article according to claim 1, wherein the absorbent material comprises from 80% to 100% by weight of superabsorbent particles.

13. The absorbent article according to claim 1, wherein the stabilization element has a length as measured in the longitudinal direction in the range of from 100 mm to 500 mm.

14. The absorbent article according to claim 1, wherein the absorbent core comprises a spunlace core wrap top layer, and wherein the basis weight of the spunlace core wrap top layer ranges from about 40 $g/m^2$ to about 200 $g/m^2$.

15. The absorbent article according to claim 1, wherein the absorbent article is an adult incontinence pant comprising a front panel, a rear panel, wherein the front panel and the rear panel are joined to each other along left and right side seams, and an absorbent pad assembly extending between the front panel and the rear panel, wherein the topsheet, backsheet and absorbent core are comprised by the absorbent pad assembly, the incontinence pant comprising a barrier leg cuff on each longitudinal edges of the absorbent assembly pad, each barrier leg cuff comprising a proximal edge attached to the topsheet and a free edge capable of standing upwards away from the topsheet.

* * * * *